US00PP36780P2

(12) United States Plant Patent
Sills et al.

(10) Patent No.: US PP36,780 P2
(45) Date of Patent: Jul. 1, 2025

(54) BLACKBERRY PLANT NAMED 'DrisBlackThirtyFour'

(50) Latin Name: ***Rubus* L.**
Varietal Denomination: DrisBlackThirtyFour

(71) Applicant: Driscoll's, Inc., Watsonville, CA (US)

(72) Inventors: Gavin R. Sills, Gilroy, CA (US); Yunwen Wang, Aptos, CA (US); Mark F. Crusha, Santa Cruz, CA (US); John Nader Fangary, Royal Oaks, CA (US)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 18/792,288

(22) Filed: Aug. 1, 2024

(51) Int. Cl.
*A01H 5/08* (2018.01)
*A01H 6/74* (2018.01)

(52) U.S. Cl.
USPC ..... Plt./203

(58) Field of Classification Search
USPC ..... Plt./203
See application file for complete search history.

(56) References Cited

U.S. PATENT DOCUMENTS

| | | | |
|---|---|---|---|
| PP6,679 | P | 3/1989 | Moore |
| PP6,782 | P | 5/1989 | Jennings |
| PP13,525 | P3 | 1/2003 | Fear et al. |
| PP13,758 | P3 | 5/2003 | Fear et al. |
| PP13,759 | P3 | 5/2003 | Fear et al. |
| PP14,682 | P3 | 4/2004 | Fear et al. |
| PP14,765 | P2 | 5/2004 | Cook et al. |
| PP14,780 | P2 | 5/2004 | Cook et al. |
| PP15,058 | P2 | 8/2004 | Cook et al. |
| PP17,162 | P3 | 10/2006 | Moore et al. |
| PP17,983 | P2 | 9/2007 | Cabrera |
| PP22,002 | P2 | 7/2011 | Pabon et al. |
| PP22,449 | P3 | 1/2012 | Clark |
| PP23,497 | P3 | 3/2013 | Clark et al. |
| PP23,725 | P3 | 7/2013 | Sills et al. |
| PP24,249 | P3 | 2/2014 | Clark |
| PP24,609 | P3 | 7/2014 | Rodriguez et al. |
| PP24,701 | P3 | 7/2014 | Rodriguez et al. |
| PP24,878 | P2 | 9/2014 | Alcazar et al. |
| PP25,502 | P3 | 5/2015 | Pabon et al. |
| PP26,501 | P3 | 3/2016 | Pabon et al. |
| PP26,611 | P3 | 4/2016 | Pabon et al. |
| PP26,774 | P3 | 5/2016 | Pabon et al. |
| PP27,129 | P2 | 9/2016 | Sills et al. |
| PP27,130 | P2 | 9/2016 | Sills et al. |
| PP27,146 | P2 | 9/2016 | Sills et al. |
| PP27,681 | P3 | 2/2017 | Sills et al. |
| PP27,746 | P3 | 3/2017 | Sills et al. |
| PP28,548 | P2 | 10/2017 | Sills et al. |
| PP31,110 | P2 | 11/2019 | Sills et al. |
| PP31,291 | P2 | 12/2019 | Sills et al. |
| PP31,825 | P2 | 6/2020 | Sills et al. |
| PP31,826 | P2 | 6/2020 | Sills et al. |
| PP32,268 | P2 | 10/2020 | Sills et al. |
| PP33,067 | P2 | 5/2021 | Sills et al. |
| PP33,068 | P2 | 5/2021 | Sills et al. |
| PP33,088 | P2 | 5/2021 | Sills et al. |
| PP34,069 | P2 | 3/2022 | Sills et al. |
| PP34,291 | P2 | 6/2022 | Sills et al. |
| PP34,320 | P2 | 6/2022 | Escobedo et al. |
| PP34,438 | P2 | 7/2022 | Sills et al. |
| PP34,481 | P2 | 8/2022 | Sills et al. |
| PP35,078 | P2 | 4/2023 | Sills et al. |
| PP35,233 | P2 | 6/2023 | Sills et al. |
| PP35,898 | P2 | 7/2024 | Sills et al. |

OTHER PUBLICATIONS

Voss, Donald H. The Royal Horticultural Society Colour Chart 2001 Journal American Rhododendron Society, vol. 56, No. 1 2002 3 pages.

Williams, et al. DNA polymorphisms amplified by arbitrary primers are useful as genetic markers Nucleic Acids Research, vol. 18, No. 22 1990 pp. 6531-6535.

*Primary Examiner* — Susan McCormick Ewoldt
(74) *Attorney, Agent, or Firm* — Morrison & Foerster LLP

(57) ABSTRACT

A new and distinct variety of blackberry plant named 'DrisBlackThirtyFour', particularly selected for its fruit flavor, firmness, shelf life, and berry size, is disclosed.

5 Drawing Sheets

Latin name: Botanical classification: *Rubus* L. subgenus *Rubus*.

Varietal denomination: The varietal denomination of the claimed variety of blackberry plant is 'DrisBlackThirty-Four'.

BACKGROUND OF THE INVENTION

Blackberry is the common name for a multitude of plant species bearing dark purple to black aggregate fruit in the genus *Rubus* of the family Rosaceae. Most blackberries are within the subgenus *Rubus*.

Native chiefly to the northern temperate regions, blackberries are now being cultivated as a valuable fruit crop in many areas of the world, particularly in Europe, North America and Central America. Recognized for their high contents of antioxidants, dietary fiber, vitamin C, and vitamin K. Blackberry fruit are typically consumed as fresh fruit, individually quick frozen fruit, or in prepared foods, such as purées, juices, jellies, jams, grocery items, baked goods, and snack foods.

Globally, Mexico is the leading producer of blackberries, with nearly the entire crop being produced for export into the off-season fresh markets in North America and Europe. The Mexican market is almost entirely from the cultivar 'Tupi' (also spelled as 'Tupy'). In the United States, Oregon is the leading commercial blackberry producer, followed by the state of California.

Blackberries are perennial plants that typically bear biennial stems (known as "canes") from a perennial root system. The two cane types are primocanes, or first-year canes, which are usually vegetative, and floricanes, which are the same canes and produce fruit in the next growing season. In its first year, a new cane, the primocane, grows vigorously to its full length of three to six meters in a growth habit of erecting, arching, or trailing along the ground and bearing large compound leaves with 3, 5, or 7 leaflets; it does not produce any flowers. In its second year, the cane becomes a floricane and stops elongating, but the lateral buds break to produce flowering laterals that bear fruit.

Recently, primocane-fruiting blackberry varieties have been developed that are capable of flowering and fruiting on first-year canes. Primocane-fruiting blackberry varieties have several advantages, including potential of two crops on the same plant in the same year, reduction in pruning costs by mowing of canes, avoidance of winter injury, and production of fruit in an extended geographic area. However, primocane-fruiting blackberry varieties are also subject to a number of challenges, such as poor heat tolerance, lesser fruit quality, and low yield.

Blackberry is an important and valuable commercial fruit crop. Accordingly, there is a need for new varieties of blackberry plant. In particular, there is a need for improved varieties of blackberry plant that are stable, high yielding, and agronomically sound.

SUMMARY OF THE INVENTION

In order to meet these needs, the present invention is directed to an improved variety of blackberry plant. In particular, the invention relates to a new and distinct variety of blackberry plant (*Rubus* L. subgenus *Rubus*), which has been denominated as 'DrisBlackThirtyFour'.

Blackberry plant variety 'DrisBlackThirtyFour' was selected in Ciudad Guzman, Jalisco, Mexico in January 2016 and originated from a controlled cross between the female parent blackberry plant 'DrisBlackThirteen' (U.S. Plant Pat. No. 27,681) and a male parent blackberry plant obtained from a bulk population designated as 'Bulk S' (unpatented). The original seedling of the new variety was first asexually propagated via root cuttings in Ciudad Guzman, Jalisco, Mexico in February 2016.

'DrisBlackThirtyFour' was subsequently asexually propagated and underwent testing in Ciudad Guzman, Jalisco, Mexico from 2016 to 2019 (three years). The present variety has been found to be stable and reproduce true to type through successive asexual propagations via root cuttings and tissue culture.

'DrisBlackThirtyFour' was selected for its fruit flavor, firmness, shelf life, and berry size.

BRIEF DESCRIPTION OF THE DRAWINGS

This new blackberry plant is illustrated by the accompanying photographs. The colors shown are as true as can be reasonably obtained by conventional photographic procedures. The photographs are of plants that are two to five years old.

DETAILED BOTANICAL DESCRIPTION

Figure 1:
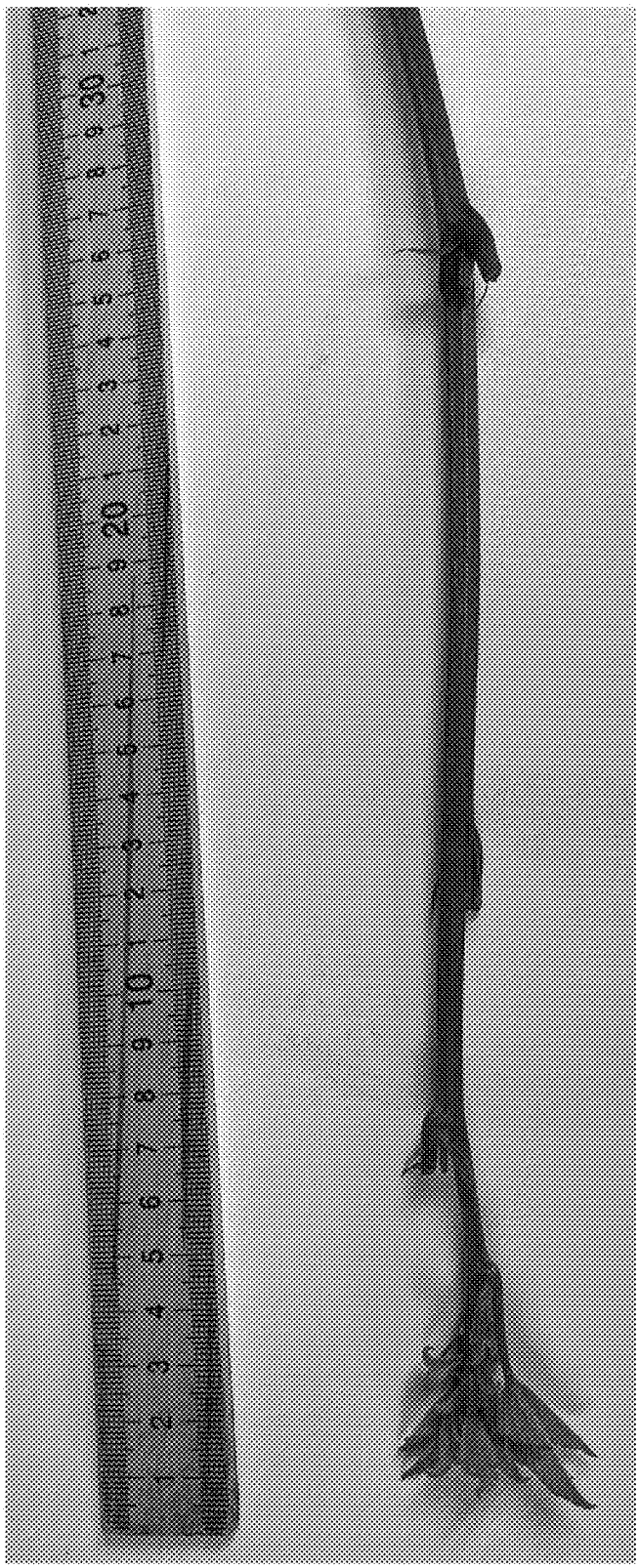
FIG. 1 illustrates a section of a cane of variety 'DrisBlackThirtyFour'.
Figure 2:
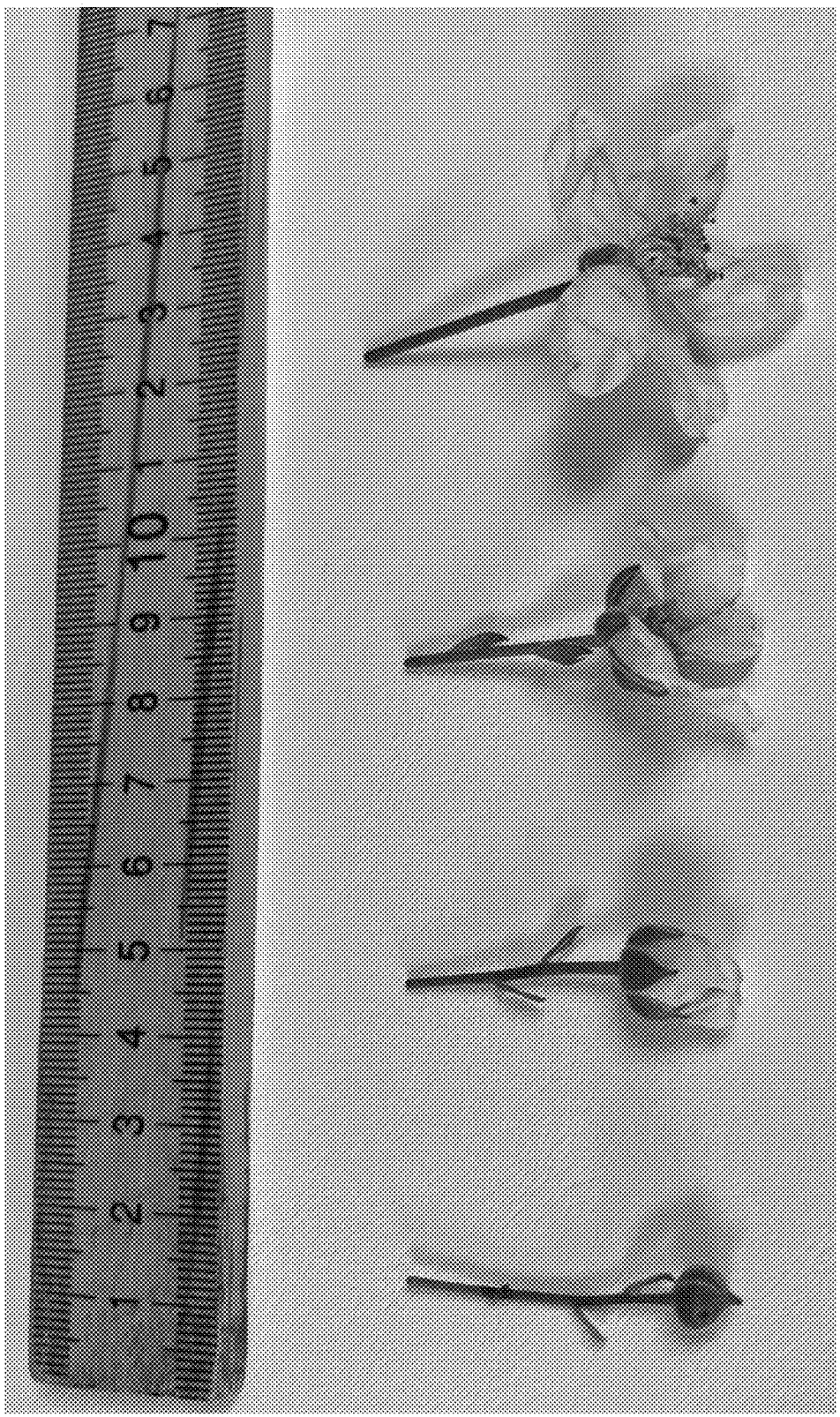
FIG. 2 illustrates flowers of variety 'DrisBlackThirtyFour' at various stages of development.
Figure 3:
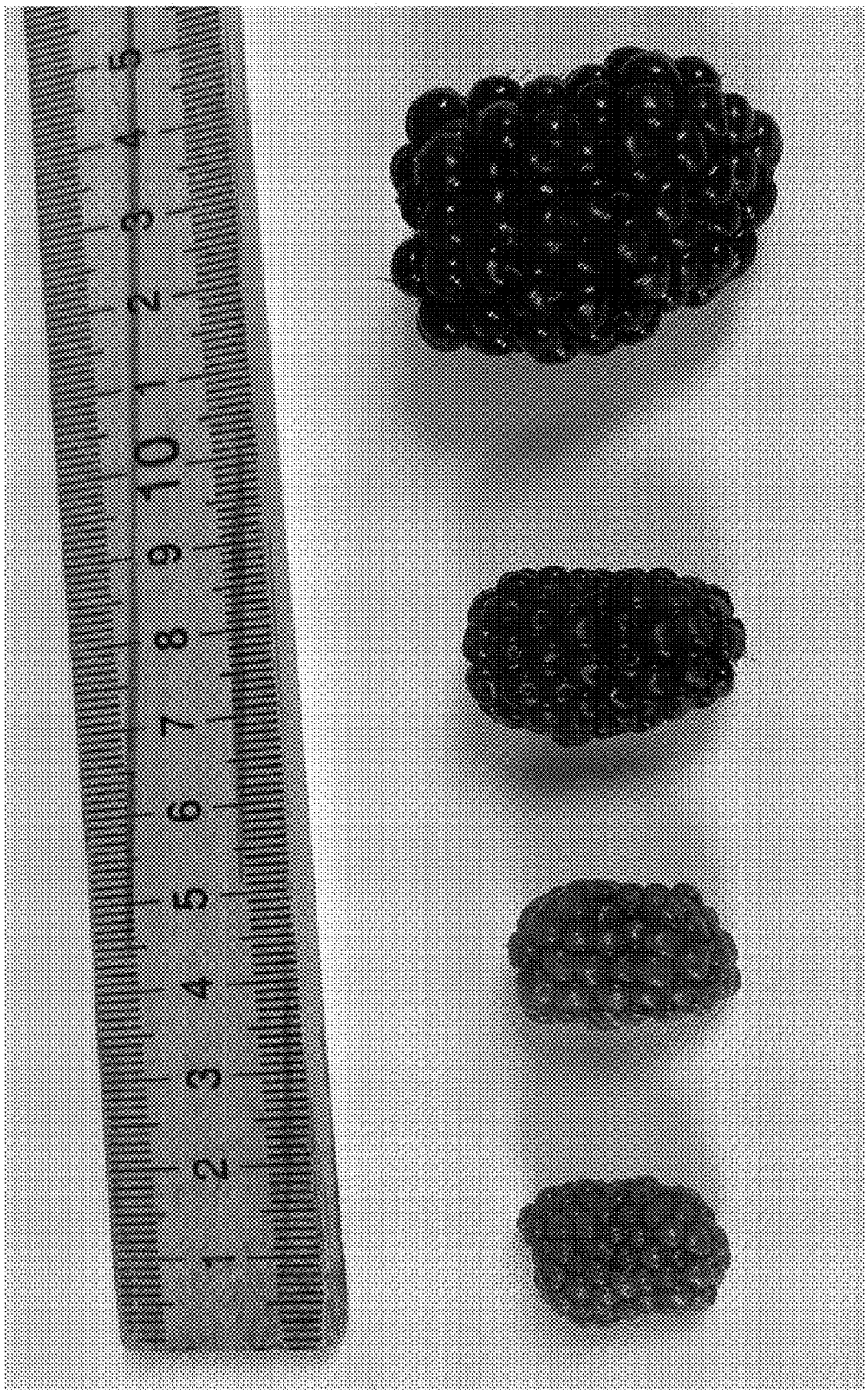
FIG. 3 illustrates fruits of variety 'DrisBlackThirtyFour' at various stages of development.
Figure 4:
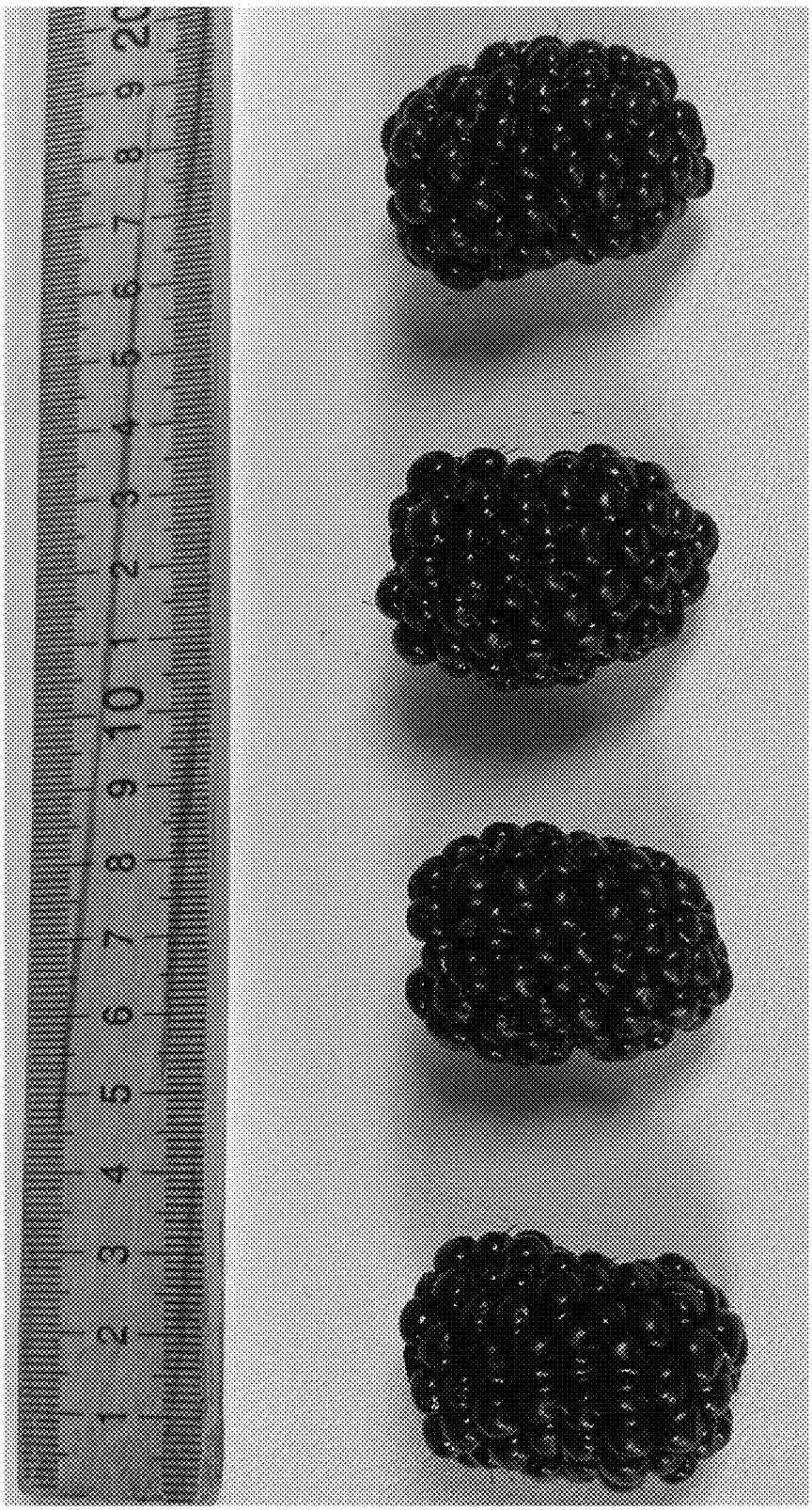
FIG. 4 illustrates ripe fruits of variety 'DrisBlackThirtyFour'.
Figure 5:
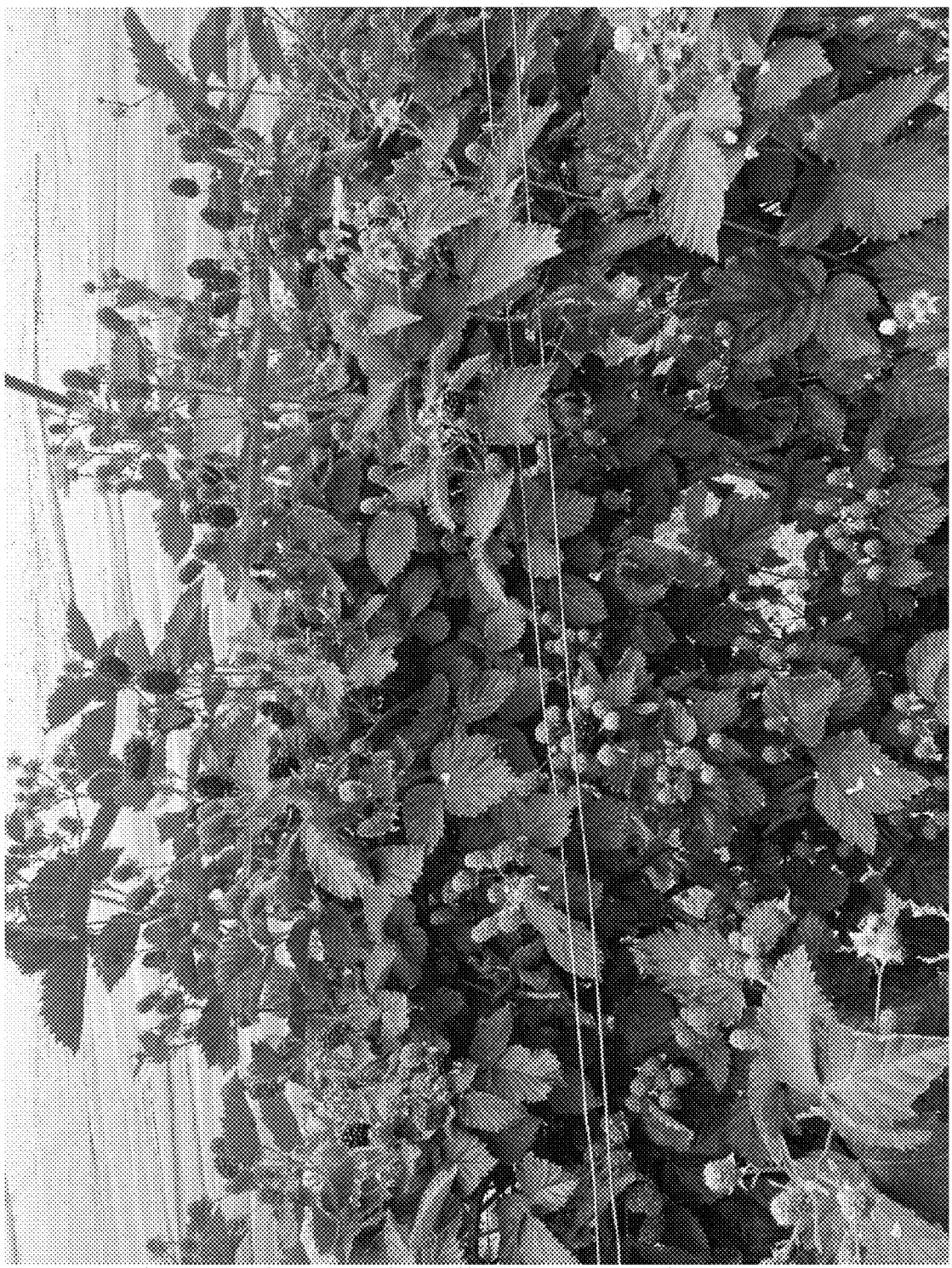
FIG. 5 illustrates a whole plant of variety 'DrisBlackThirtyFour'.

The following descriptions set forth the distinctive characteristics of 'DrisBlackThirtyFour'. The data that define these characteristics are based on observations taken in Ciudad Guzman, Jalisco, Mexico from 2016 to 2019. This description is in accordance with UPOV terminology. Color designations, color descriptions, and other phenotypical descriptions may deviate from the stated values and descriptions depending upon variation in environmental, seasonal, climatic and cultural conditions. 'DrisBlackThirtyFour' has not been observed under all possible environmental conditions. The botanical description of 'DrisBlackThirtyFour' was taken from plants that were two to five years old. The indicated values represent averages calculated from measurements of several plants. Color references are primarily to The R.H.S. Colour Chart of The Royal Horticultural Society of London (R.H.S.) (2015 edition). Descriptive terminology follows the *Plant Identification Terminology, An Illustrated Glossary,* $2^{nd}$ edition by James G. Harris and Melinda Woolf Harris, unless where otherwise defined.

Classification:

*Family*.—Rosaceae.

*Botanical*.—*Rubus* L. subgenus *Rubus*.

*Common name*.—Blackberry.

*Variety name*.—'DrisBlackThirtyFour'.

Parentage:

*Female parent*.—'DrisBlackThirteen' (U.S. Plant Pat. No. 27,681).

*Male parent*.—'Bulk S' (unpatented).

Plant:

*Propagation*.—Root cuttings and tissue culture.

*Growth habit*.—Upright.

*Height*.—186 cm.

*Width*.—94 cm.

*Height/width ratio*.—1.98.

*Self-fruitfulness*.—Self-fruitful.

Canes:

*Internodal distance*.—7 cm.

*New cane*.—Glaucosity (waxy bloom): Medium.

*Dormant cane*.—Anthocyanin coloration: Medium. Overall coloration: RHS 144A (Strong yellow green). Predominant distribution of branches: Only on upper half. Cross-section: Angular. Spine: Presence of spines: Absent.

*Fruiting lateral*.—Fruiting lateral length ($4^{th}$ lateral from tip): 38 cm. Number of fruits per fruiting lateral: 12.6.

*Young shoots*.—Length: 121 cm. Diameter: 1 cm. Anthocyanin coloration (during rapid growth): Strong. Overall color: RHS 143B (Strong yellow green). Number of glandular hairs: Absent or few. Time of young shoot emergence: February to March.

Leaves:

*Time of leaf bud burst*.—Mid-March.

*Leaf*.—Predominant number of leaflets: Five (5). Type: Palmate. Relative position of lateral leaflets: Overlapping. Arrangement: Whorled. Venation: Cross-venulate. Vein color: RHS 143C (Strong yellow green). Color of upper side: RHS 141A (Deep yellowish green). Color of lower side: RHS 143A (Strong yellow green). Profile in cross-section: Concave (margins rolled inwards). Glossiness of upper side: Medium.

*Leaflet*.—Type of incision of margin: Bi-serrate. Depth of margin incisions: Medium.

*Terminal leaflet*.—Length: 10.6 cm. Width: 8 cm. Length/width ratio: 1.3. Shape: Oval. Base: Obtuse. Margin: Doubly serrate. Lobing: Absent. Shape in cross-section: U-shaped. Undulation of margin: Absent or very weak. Blistering between veins: Medium.

*Lateral leaflet* (*single leaflet in basal pair*).—Length: 10 cm. Width: 8 cm. Length/width ratio: 1.25. Shape: Oval. Base: Obtuse. Margin: Doubly serrate.

*Rachis* (*length between terminal leaflet and adjacent lateral leaflets*).—3 cm.

*Petiole*.—Length: 7 cm. Diameter: 3 mm. Color of upper surface: RHS 143B (Strong yellow green). Color of lower surface: RHS 144A (Strong yellow green).

*Stipule*.—Length: 1 cm. Width: 2 mm. Color: RHS 143A (Strong yellow green). Orientation: Erect.

Inflorescence:

*Flower bud*.—Length: 6.7 mm. Width: 7.4 mm. Color: RHS 143C (Strong yellow green).

*Flower*.—Diameter: 38 mm. Number of flowers observed at 3$^{rd}$ node from tip of lateral: 7.8. Fragrance: Very faint or absent.

*Petal*.—Length: 18 mm. Width: 10.4 mm. Length/width ratio: 1.73.Number of petals per flower: 5. Color of upper surface: RHS 69D (Very pale purple). Color of lower surface: RHS 69D (Very pale purple). Shape: Oval. Apex: Rounded. Base: Obtuse. Margin: Erose.

*Sepal*.—Length: 7 mm. Width: 6 mm. Average number of sepals per flower: 5. Color: RHS 143B (Strong yellow green).

*Flower pedicel*.—Length: 60 mm. Diameter: 1 mm. Color: RHS 143A (Strong yellow green).

*Inflorescence peduncle*.—Length: 108 mm. Diameter: 1 mm. Color: RHS 143A (Strong yellow green).

*Reproductive organs*.—Style: Length: 2 mm. Color: RHS 144C (Strong yellow green). Ovary: Color: RHS 144A (Strong yellow green). Stamen: Length: 6.5 mm. Color: RHS 144B (Strong yellow green). Pollen: Amount: Medium. Color: RHS 145C (Light yellow green).

*Flowering interval on previous year's cane* (*floricane*) .—April to June.

Fruit:

*Length of mature fruit*.—37 mm.

*Diameter of mature fruit*.—26 mm.

*Ratio of length to width*.—1.03.

*Floricane fruit weight*.—10 g/fruit.

*Sweetness/soluble solids* (*in ° Brix*).—13.

*Titratable acidity* (*% as citric acid*).—1.7%.

*Glossiness*.—Medium.

*Firmness*.—Medium.

*Fruit shape in longitudinal section*.—Narrow ovate.

*Fruit color*.—RHS 203A (Black).

*Drupe*.—Length of single drupe: 5 mm. Diameter of single drupe: 4 mm. Average number of drupes per fruit: 100.

*Seed*.—Diameter: 1 mm. Weight: 0.0039 g/seed. Color: RHS 156A (Greyed-white). Abundance: Medium.

*Fruiting on current year's cane*.—Absent.

*Harvest interval on previous year's cane* (*floricane*).—June to late July.

*Storage/shipping characteristics*.—Following harvest, fruit can be stored for 7 to 10 days if maintained under cooled temperatures that are standard for blackberry storage.

*Yield*.—9,000 lbs to 15,000 lbs of fruit per acre per season from 24-to 36-month-old plants when grown in Watsonville, California.

Resistance to pests and diseases:

*Fusarium wilt* (*fusarium oxysporum*).—Moderately resistant.

*Verticillium wilt* (*verticillium spp.*).—Moderately susceptible.

COMPARISON TO PARENTAL AND REFERENCE BLACKBERRY VARIETIES

'DrisBlackThirtyFour' differs from the female parent 'DrisBlackThirteen' (U.S. Plant Pat. No. 27,681) in that 'DrisBlackThirtyFour' has an upright growth habit, strong anthocyanin coloration on young shoots during rapid growth, U-shaped cross-section of terminal leaflets, and narrow ovate shape of fruit in longitudinal section, whereas 'DrisBlackThirteen' has a semi-upright growth habit, weak anthocyanin coloration on young shoots during rapid growth, V-shaped cross-section of terminal leaflets, and medium ovate shape of fruit in longitudinal section. Furthermore, 'DrisBlackThirtyFour' does not fruit on current year's cane, whereas 'DrisBlackThirteen' does fruit on current year's cane.

'DrisBlackThirtyFour' differs from the proprietary male parent 'Bulk S' (unpatented) in that fruit of 'DrisBlackThirtyFour' has improved flavor compared to 'Bulk S'.

'DrisBlackThirtyFour' differs from the reference variety 'DrisBlackTwentyThree' (U.S. Plant Pat. No. 33,067) in that 'DrisBlackThirtyFour' has strong anthocyanin coloration on young shoots during rapid growth, medium anthocyanin coloration on dormant canes, medium intensity of green color of upper side of leaves, medium blistering between veins on terminal leaflets, and narrow ovate shape of fruit in longitudinal section, whereas 'DrisBlackTwentyThree' has medium anthocyanin coloration on young shoots during rapid growth, strong anthocyanin coloration on dormant canes, dark intensity of green color of upper side of leaves, weak blistering between veins on terminal leaflets, and elliptic shape of fruit in longitudinal section.

'DrisBlackThirtyFour' differs from the reference variety 'DrisBlackTwenty' (U.S. Plant Pat. No. 31,826) in that 'DrisBlackThirtyFour' has medium anthocyanin coloration on dormant canes, U-shaped cross-section of terminal leaflets, medium time of beginning of flowering on previous year's cane, medium fruit width, and narrow ovate shape of fruit in longitudinal section, whereas 'DrisBlackTwenty' has absent or very weak anthocyanin coloration on dormant canes, V-shaped cross-section of terminal leaflets, early time of beginning of flowering on previous year's cane, very broad fruit width, and medium ovate shape of fruit in longitudinal section.

What is claimed is:

1. A new and distinct variety of blackberry plant designated 'DrisBlackThirtyFour' as shown and described herein.

* * * * *